United States Patent [19]

Rentzea et al.

[11] Patent Number: 5,019,598

[45] Date of Patent: May 28, 1991

[54] AMINOMETHYLPHENOLS AND FUNGICIDES CONTAINING THESE COMPOUNDS

[75] Inventors: Costin Rentzea, Heidelberg; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 366,458

[22] Filed: Jun. 15, 1989

[30] Foreign Application Priority Data

Jun. 15, 1988 [DE] Fed. Rep. of Germany ....... 3820292

[51] Int. Cl.⁵ .................. H01N 33/04; C07C 211/33; C07C 211/34; C07C 211/35
[52] U.S. Cl. .................... 514/650; 514/655; 564/387; 564/390; 564/389
[58] Field of Search ........ 564/389, 390, 387; 514/655, 650

[56] References Cited

U.S. PATENT DOCUMENTS

| | | | |
|---|---|---|---|
| 2,192,927 | 3/ | Morrill | 564/384 X |
| 2,262,720 | 11/1941 | Earle | 564/389 X |
| 2,795,613 | 6/1957 | Walter et al. | 260/570.9 |
| 4,073,942 | 2/1978 | Keck et al. | 424/330 |
| 4,113,777 | 9/1978 | Keck et al. | 260/570.9 |

FOREIGN PATENT DOCUMENTS 542192  6/1957  Canada ................ 564/390

Primary Examiner—Richard L. Raymond
Attorney, Agent, or Firm—Oblon, Spivak, McClelland, Maier & Neustadt

[57] ABSTRACT o-Aminomethylphenols of the formula

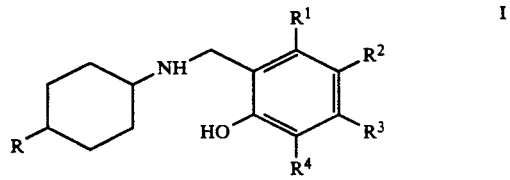

where $R^1$, $R^3$ and $R^4$ are hydrogen, fluorine, chlorine, bromine, alkyl, alkoxy or dimethylamino, $R^2$ is hydrogen, chlorine, bromine, alkyl, alkenyl, alkoxyalkyl, cyclohexyl or phenyl, or $R^1$ and $R_2$, $R^2$ and $R^3$ or $R^3$ and $R^4$ form a carbocyclic, saturated or unsaturated five-membered or six-membered ring, and R is alkyl, and salts thereof, and fungicides containing these compounds.

8 Claims, No Drawings

AMINOMETHYLPHENOLS AND FUNGICIDES CONTAINING THESE COMPOUNDS

The present invention relates to novel, substituted o-aminomethylphenols having a fungicidal action, their preparation, fungicides which contain these phenols as active ingredients, and their use for controlling harmful fungi.

It is known that N-tridecyl-2,6-dimethylmorpholine can be used as a fungicide (DE-11 64 152).

We have found that novel substituted o-aminomethylphenols of the formula I

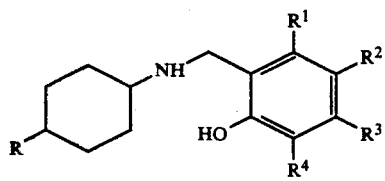

where $R^1$, $R^3$ and $R^4$ are each hydrogen, fluorine, chlorine, bromine, $C_1$-$C_4$-alkyl, $C_1$-$C_4$-alkoxy or dimethylamino, $R^2$ is hydrogen, chlorine, bromine, $C_1$-$C_{10}$-alkyl, $C_3$-$C_8$-alkenyl, alkoxyalkyl, cyclohexyl or phenyl, or $R^1$ and $R^2$, $R^2$ and $R^3$ or $R^3$ and $R^4$ form a carbocyclic, saturated or unsaturated five-membered or six-membered ring, and R is $C_1$-$C_5$-alkyl which may have either a trans or a cis configuration with respect to the nitrogen atom, and their salts have excellent activity against harmful fungi and are well tolerated by plants.

The radicals $R^1$, $R^2$, $R^3$ and $R^4$ may be identical or different.

The novel o-aminomethylphenols of the formula I may contain chiral centers. They are obtained in general as racemates and may be obtained in the form of diastereomer mixtures. Isomers having a single configuration can be isolated by known methods. All these compounds and mixtures are embraced by the present invention. Regarding the use or the novel o-aminomethylphenols as fungicides, both the pure diastereomers, enantiomers or cis/trans isomers and their mixtures obtained in the synthesis are suitable as fungicides. The mixtures are preferably used.

$C_1$-$C_4$-alkyl radicals $R^1$ are, for example, methyl, ethyl, propyl and butyl.

$C_1$-$C_4$-alkoxy radicals $R^1$ are, for example, methoxy, ethoxy, propoxy and butoxy.

$C_1$-$C_{10}$-alkyl radicals $R^2$ are, for example, methyl, ethyl, propyl, butyl, pentyl, hexyl, heptyl, octyl, nonyl and decyl, in particular tert-butyl.

$C_3$-$C_8$-alkenyl radicals $R^2$ are, for example, allyl, methallyl and butenyl, and alkoxyalkyl radicals $R^2$ are, for example, $C_1$-$C_4$-alkoxy-$C_1$-$C_4$-alkyl, eg. methoxymethyl, methoxyethyl and ethoxyethyl. $R^1$ and $R^2$ together form a carbocyclic, saturated or unsaturated five-membered or six-membered ring, ie. the ring is formed together with the two carbon atoms of which $R^1$ and $R^2$ are substituents.

If $R^1$ and $R^2$ are, for example, the radical —$C_3H_6$—, they form, together with the two abovementioned carbon atoms, a five-membered ring having 5 carbon atoms in the ring.

$C_1$-$C_5$-alkyl radicals R are, for example, methyl, ethyl, propyl, butyl and pentyl, in particular tertbutyl.

The o-aminomethylphenols of the formula I can be prepared, for example, by a) reacting a salicylaldehyde of the formula II with an amine of the formula III

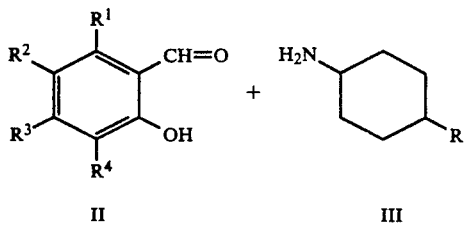

where R, $R^1$, $R^2$, $R^3$ and $R^4$ have the abovementioned meanings, in the presence of formic acid, of sodium cyanoborohydride or of sodium borohydride or in the presence of hydrogen and a hydrogenation catalyst, such as Ni, Pd or Pt, or b) reacting a phenol of the formula IV with formaldehyde and with an amine of the formula III

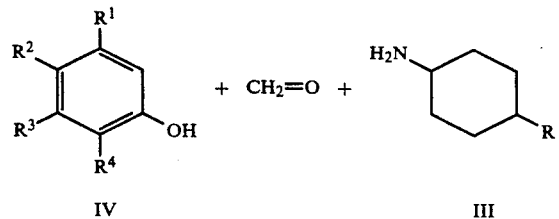

where R, $R^1$, $R^2$, $R^3$ and $R^4$ have the abovementioned meanings, in the presence of a basic catalyst, and, if necessary, converting the resulting compounds into its salts.

In process variant a), amines of the formula III are reacted with aldehydes of the formula II, for example in the presence of formic acid. This reductive alkylation is preferably carried out in the absence of a solvent. The aldehyde is added dropwise to a solution of the amine in formic acid at from 0° C. to 110° C., preferably from 50° to 100° C.

The reactions of the aldehydes with amines of the formula III are carried out in the presence of sodium borohydride or sodium cyanoborohydride, for example in a solvent or diluent. Alcohols, such as methanol, ethanol, propanol and isopropanol, which contain up to 25% by volume of water, are preferred for this purpose.

In process variant a), it is also possible to alkylate amines of the formula III with aldehydes of the formula II in the presence of hydrogen and a hydrogenation catalyst, for example under a hydrogen pressure of from 1 to 150 bar and at from 25° to 120° C.

Suitable catalysts are noble metals, for example palladium, platinum, if necessary deposited on a carrier, and rhodium and nickel (Raney nickel). Palladium on carbon is preferred. Suitable solvents are alcohols, such as methanol or ethanol, and hydrocarbons, such as hexane, heptane, octane, cyclohexane, toluene and xylene.

Examples of suitable solvents or diluents for this process variant are halohydrocarbons, in particular chlorohydrocarbons, eg. tetrachloroethylene, 1,1,2,2- and 1,1,1,2-tetrachloroethane, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cisdichloroethylene, chlorobenzene, fluorobenzene, bromobenzene, iodobenzene, o-, m- and p- dichlorobenzene, o-, p- and m-dibromobenzene, o-, m- and p-chlorotoluene and 1,2,4-trichlorobenzene; ethers, eg. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, ethylene glycol dimethyl ether, tetrahydrofuran, dioxane, thioanisole and $\beta, \beta, \beta'$-dichlorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic or cycloaliphatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; ketones, eg. acetone, methyl ethyl ketone, water and possibly even mixtures of these solvents.

The following bases are suitable for process variant b): potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, tripropylamine, tributylamine, triisobutylamine,tri-sec-butylamine,tri-tertbutylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyl-toluidine,N,N-dipropyltoluidine,N,N-dimethyl-p-aminopyridine, N,N-diethyl-p-aminopyridine, N,N-dipropyl-p-aminopyridine, N-methylpyrrolidine, N-ethylpyrrolidone, N-methylimidazole, N-ethylimidazole, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline,N-propyldiisopropylamine,N,N-dimethylcyclohexylamine, 2,6-lutidine, 2,4-lutidine, trifurylamine and triethylenediamine.

Solvents such as water, methanol, ethanol, tetrahydrofuran, dioxane or mixtures of these are preferably used for this purpose.

Process variant b) is carried out, for example, at from 10° to 150° C.

Provided that they form phytophysiologically tolerated salts, all organic or inorganic acids are suitable for salt formation with compounds of the formula I. Examples are chlorides, bromides, iodides, sulfates, phosphates, acetates, oxalates, fumarates, malonates, alkylsulfonates, arylsulfonates and dodecylbenzenesulfonates.

The salts are obtained by combining the corresponding acid with a free amine of the formula I, if necessary in an inert solvent, separating off the solvent and if necessary recrystallizing the residue.

The starting materials for the formulae II, III and IV are known and/or can be prepared by a conventional method.

The Examples which follow illustrate the preparation of the compound of the formula I:

EXAMPLE 1

Trans-2-(4'-tert-butylcyclohexylamino)-methyl-4-tert-pentylphenol 41 3 ml (0.55 mole) of 37% strength aqueous formaldehyde solution, 85.3 g (0.55 mole) of trans-4-tertbutyl-cyclohexylamine, 95 g (0.579 mole) of 4-tert-pentyl-phenol and 1 g of sodium hydroxide are added in succession to 300 ml of dioxane at from 20° to 35° C. The mixture is then stirred for 6 hours at 70° C. and cooled to +5° C., and the precipitate is filtered off under suction, washed with 100 ml of water and then with 50 ml of dioxane and dried. 104 g (57% of theory) of trans-2-(4'-tert-butylcyclohexylamino)-methyl-4-tert-pentyl-phenol are obtained as white crystals of melting point 148°–150° C. (active ingredient No. 1).

The compounds of the formula I which are listed below can be obtained correspondingly by selecting the starting materials and appropriately adapting the process conditions:

| Ex. No. | R (trans/cis) —C(CH₃)₃ | R¹ | R² | R³ | R⁴ | Salt (Acid) | Mp °C. |
|---|---|---|---|---|---|---|---|
| 2 | trans | H | —CH₂—CH₂—CH₂— | | H | — | 128–130 |
| 3 | trans | H | —C(CH₃)₃ | H | H | — | 161–163 |
| 4 | trans | H | —C(CH₃)₃ | H | —CH₃ | (HCl) | 248–250 |
| 5 | cis | H | cyclohexyl | H | H | — | 131–134 |
| 6 | trans | H | cyclohexyl | H | H | — | 146–148 |
| 7 | trans | H | phenyl | H | H | — | 147–149 |
| 8 | cis | H | phenyl | H | H | — | 135–137 |
| 9 | trans | H | —CH(CH₃)₂ | H | H | — | 125–127 |
| 10 | cis | H | —CH(CH₃)₂ | H | H | — | 115–117 |
| 11 | cis | H | —C(CH₃)₂CH₂CH(CH₃)₂ | H | H | — | 172–175 |
| 12 | cis | H | —C(CH₃)₂CH₂C(CH₃)₃ | H | H | — | 174–176 |
| 13 | trans | H | —CH₂—CH₂—O—CH₃ | H | H | — | 73–75 |
| 14 | trans | H | H | —N(CH₃)₂ | H | — | |
| 15 | trans | H | Cl | H | H | — | 130–132 |
| 16 | trans | H | F | H | H | — | 114–115 |
| 17 | trans | H | Cl | Cl | H | — | 175–178 |
| 18 | trans | H | —C₂H₅ | H | H | — | |
| 19 | trans | H | —CH₃ | H | —CH₃ | — | |
| 20 | trans | H | —CH₃ | CH₃ | H | — | |
| 21 | trans | H | —C₃H₇-n | H | H | — | |
| 22 | trans | H | —C₄H₉-n | H | H | — | |
| 23 | trans | H | —C₄H₉-i | H | H | — | |
| 24 | trans | H | —C₄H₉-sec | H | H | — | |

-continued

| Ex. No. | R (trans/cis) —C(CH$_3$)$_3$ | R$^1$ | R$^2$ | R$^3$ | R$^4$ | Salt (Acid) | Mp °C. |
|---|---|---|---|---|---|---|---|
| 25 | trans | H | —C$_5$H$_{11}$-n | H | H | — | |
| 26 | trans | H | —C$_6$H$_{13}$-n | H | H | — | |
| 27 | trans | H | Br | H | H | — | |
| 28 | trans | H | Cl | H | H | — | |
| 29 | trans | H | Cl | H | H | — | |
| 30 | trans | H | —CH=CH—CH=CH— | | | — | 120–123 |
| 31 | (trans)CH$_3$ | H | —C(CH$_3$)$_3$ | H | H | — | |
| 32 | (trans)CH$_3$ | H | —CH(CH$_3$)$_2$ | H | H | — | |
| 33 | (trans)CH$_3$ | H | —C(CH$_3$)$_2$CH$_2$CH$_3$ | H | H | — | |
| 34 | (trans)CH$_3$ | H | cyclohexyl | H | H | — | |
| 35 | (trans)CH$_3$ | H | phenyl | H | H | — | |
| 36 | (trans)CH$_3$ | H | F | H | H | — | |
| 37 | (trans)CH$_3$ | H | Cl | H | H | — | |
| 38 | (trans)CH$_3$ | H | Br | H | H | — | |
| 39 | (trans)CH$_3$ | H | CH$_3$ | H | CH$_3$ | — | |
| 40 | (trans)CH$_3$ | H | Cl | H | CH$_3$ | — | |

In general terms, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats. rice, indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals.
*Rhizoctonia* species in cotton and lawns,
*Venturia inaequalis* (scab) in apples,
*Helminthosporium* species in cereals.
*Septoria nodorum* in wheat.
*Botrytis cinerea* (gray mold) in strawberries and grapes.
*Cercospora arachidicola* in groundnuts.
*Pseudocercosporella herpotrichoiides* in wheat and barley,
*Pyricularia oryzae* in rice,
*Phytophthora infestans* in potatoes and tomatoes,
*Fusarium* and *verticillium* species in various plants,
*Plasmopara viticola* in grapes,
*Alternaria* species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics e.g., xylene), chlorinated aromatics (e.g., chlorobenzenes, paraffins e.g., crude oil fractions), alcohols e.g., methanol. butanol), ketones (e.g., cyclohexanone), amines (e.g., ethanolamine, dimethylformamide), and water; carriers such as ground natural minerals (e.g., kaolins, aluminas, talc and chalk and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates; and dispersants such as lignin, sulfite waste liquors and methyicellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecllomyces variotii.

The agents and the ready-to-use formulations prepared from them, such as solutions, emulsions, suspensions, powders, dusts, pastes and granules, are applied in conventional manner, for example by spraying. atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene. 10 parts by weight of the adduct of 8 to 10 moles of ethylene oxide and 1 mole of oleic acid-Nmonoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 3 is dissolved in a mixture consisting of 40 parts by weight of cyclohexanone. 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 6 is well mixed with 3 paris by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 7 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate.
manganese zinc ethylenediaminebisdithiocarbamate,
tetramethylthiuram disulfides,
ammonia complex of zinc N,N'-ethylenebisdithiocarbamate.
ammonia complex of zinc N,N'-propylenebisdithiocarbamate.
zinc N,N'-propylenebisdithiocarbamate and
N,N'-polypropylenebisthiocarbamyl) disulfide;
nitro derivatives, such as
dinitrol(1-methylheptyl-phenyl crotonate.
2-sec-butyl-4,6-dinitrophenyl 3,3-dimethylacryiate,
2-sec-butyl-4.6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine.
O,O-diethyl phthalimidophosphonothioate,
5-amino-1-[-bis-(dimethylamino-phosphinyl]-3-phenyl-1,2,4-triazole,
2,3-dicyano-1,4-dithioanthraquinone.
2-thio-1,3-dithio[4,5-b]quinoxaline.
methyl 1-(butylcarbamyl)2-benzimidazolecarbamate.
2-methoxycarbonylaminobenzimidazole.
2-(fur-2-yl)-benzimidazole,
2-thiazol-4-yl)benzimidazole,
N-(1,1,2,2-tetrachloroethylthio-tetrahydrophthalimide,
N-trichloromethylthiotetrahydrophthalimlde.
N-trlchloromethylthiophthalimide.
N-dichlorofluoromethylthio-N', N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4(2-chlorophenylhydrazono-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilldo-6-methyl-1,4-oxathiyne 4,4-dioxide.
2-meihylfuran-3-carboxanilide.
3 2, 5-dimethylfuran-3-carboxanilide.
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzaniiide,
2-iodobenzanilide.
N-formyl-N-morpholine-2,2,2-trichloroethylacetal,
piperazine-1,4-diylbis-(1-(2,2,2-trichloroethyl)-formamide.
1-(3,4-dichloroanllino)-1-formylamino-2,2,2-trichloroethane,
2,6-dimethyl-N-tridecylmorpholine and its salts,
2,6-dmethyl-N-cyclododecylmorpholine and its salts.
N-[3-(p-tert.-butylphenyl)-2-methylpropyl]-cis-2,6-dimethylmorpholine.
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-2.4-dichlorophenyl)-4-n-propyl-1,3-dioxolan-2-ylethyl]-1H-1,2,4-triazole,
N-(n-propyl-N-2,4,6-trichlorophenoxyethyl-N'-imidazolyl-urea,
1-(4-chlorophenoxy-3,3-dimethyl-1-(1H-1,2,4-triazol-1-yl)-butan-2-one,
1-(4-chlorophenoxy-3,3-dimethyl-1-(1H-1,2,4-triazol-1-yl)-butan-2-ol,
α-(2-chlorophenyl-α-(4-chlorophenyl)-5-pyrimidinemethanol,
5-butyl-Z-dimethylamino-4-hydroxy-6-methylpyrimidine,
bis-(p-chlorophenyl-3-pyridinemethanol,
1,2-bis-3-ethoxycarbonyl-2-thioureido-benzene,
1,2-bis-3-methoxycarbonyl-2-thioureido)-benzene.
and various fungicides, such as
dodecylguanidine acetate.
3-[3-(3,5-dimethyl-2-oxycyclohexyl)-2-hydroxyethyl]-glutaramide, hexachlorobenzene.
DL-methyl-N-(2,6-dimethylphenyl)-N-fur-2-yl alanate.
methyl DL-N-(2,6-dmethylphenyl)-N-(2'-methoxyacetyl-alanate, N-2,6-dimethylphenyl-N-chloroacetyl-DL-2-aminobutyrolactone, methyl DL-N-(2,6-dimethylphenyl-N-(phenylacetyl)-alanate, 5-methyl-5-vinyl-3-(3,5-dichlorophenyl)-2,4-dioxo-1,3-oxazolidine.

3-[3,5-dichlorophenyl]-5-methyl-5-methoxymeihyl-1,3-oxazolidlne-2,4-dione.

3-[3,5-dichlorophenyl-1-isopropylcarbamylhydantoin.

N-3,5-dichlorophenyl)-1,2-dimethylcyclopropane-1,2-dicarboximide, 2-cyano-[N-(ethylaminocarbonyl-2-methoximinoj-acetamide, 1[-2,4-dichlorophenyl)-pentyl]-1H-1,2,4-triazole, 2,4-difluoro-α-(1H-1,2,4-triazol-1-ylmethyl)-benzhydryl alcohol.

N-(3-chloro-2,6-dinitro-4-trifluoromethylphenyl-5-trifluoromethyl-3-chloro-2-aminopyridine, and 1-((bis-(4-fluorophenyl)-methylsilyl)-methyl)-1H-1,2,4-triazole.

Use examples

The compound N-tridecyl-2,6-dimethylmorpholine (A) disclosed in DE-A- 11 64 152 was used for comparison purposes.

Use Example 1

Action on Plasmopara viticola

Leaves of potted vines of the Müller-Thurgau variety were sprayed with aqueous suspensions containing dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 1, 2, 3, 4, 6 and 7, applied as 0.05wt % spray liquors, had a better fungicidal action (97%) than prior art comparative agent A (65%).

Use Example 2

Action on *Botrytis cinerea* in pimientos

Pimiento seedlings of the "Neusiedler ldeal Elite" variety with 4 to 5 well developed leaves were sprayed to runoff with aqueous suspensions containing dry basis) 80% of active ingredient and 20% of emulsifier. After the sprayed-on layer had dried, the plants were sprayed with a conidial suspension of the fungus Botrytis cinerea and kept in a high-humidity chamber at 22° to 24° C. After 5 days, the disease had spread on the untreated control plants to such an extent that the necroses covered the major portion of the leaves.

The results show that active ingredients 1, 2 and 6, applied as 0.05% spray liquors, had a better fungicidal action (97%) than prior art comparative agent A 20%).

We claim:

1. A compound of the formula I

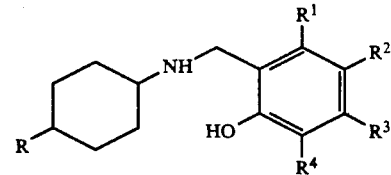

where $R^1$, $R^3$ and $R^4$ are hydrogen, fluorine, chlorine, bromine, $C_1$–$C_4$-alkyl, $C_1$–$C_4$-alkoxy or dimethylamino, $R^2$ is hydrogen, chlorine, bromine, $C_1$–$C_{10}$-alkyl, $C_3$–$C_8$-alkenyl, $C_1$–$C_4$-alkoxy-$C_1$–$C_4$-alkyl, cyclohexyl or phenyl, or $R^1$ and $R^2$, $R^2$ and $R^3$ or $R^3$ and $R^4$ form a carbocyclic, saturated or unsaturated five-membered or six-membered ring, and R is $C_1$–$C_5$-alkyl, and salts thereof.

2. A compound of the formula 1 as set forth in claim 1, where $R^1$, $R^3$ and $R^4$ each denote hydrogen, $R^2$ is tert-pentyl and R is tert-butyl.

3. A compound of the formula 1 as set forth in claim 1, where $R^1$, $R^3$ and $R^4$ each denote hydrogen, and $R^2$ and R each denote tert-butyl.

4. A compound of the formula 1 as set forth in claim 1, where $R^1$, $R^3$ and $R^4$ each denote hydrogen, $R^2$ denotes cyclohexyl and R is tert-butyl.

5. A compound of claim 1 wherein R is tert-butyl.

6. A compound of claim 1 wherein R is trans-$C(CH_3)_3$; $R^1$ is hydrogen; $R^4$ is hydrogen; and $R^2$ and $R^3$ together are —$(CH_2)_3$—.

7. A fungicidal agent containing a fungicidally effective amount of a compound of the formula I

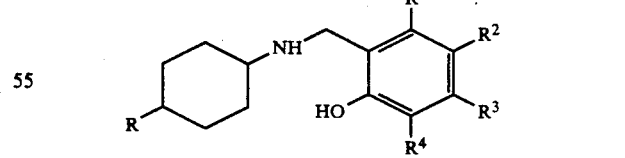

where $R^1$, $R^3$ and $R^4$ are hydrogen, fluorine, chlorine, bromine, $C_1$–$C_4$-alkyl, $C_1$–$C_4$-alkoxy or dimethylamino, $R^2$ is hydrogen, chlorine, bromine, $C_1$–$C_{10}$-alkyl, $C_3$–$C_8$-alkenyl, $C_1$–$C_4$-alkoxy-$C_1$–$C_4$-alkyl, cyclohexyl or phenyl, or $R^1$ and $R^2$, $R^2$ and $R^3$ or $R^3$ and $R^4$ form a carbocyclic, saturated or unsaturated five-membered or six-membered ring, and R is $C_1$–$C_5$-alkyl, or a salt thereof, and a solid or liquid carrier.

8. A process for combating fungi, wherein a fungicidally effective amount of a compound of the formula I where $R^1$, $R^3$ and $R^4$ are hydrogen, fluorine, chlorine, bromine, $C_1$–$C_4$-alkyl, $C_1$–$C_4$-alkoxy or dimethylamino, $R^2$ is hydrogen, chlorine, bromine, $C_1$–$C_{10}$-alkyl, $C_3$–$C_8$-alkenyl, $C_1$–$C_4$-alkoxy-$C_1$–$C_4$-alkyl, cyclohexyl or phenyl, or $R^1$ and $R^2$, $R^2$ and $R^3$ or $R^3$ and $R^4$ form a carbocyclic, saturated or unsaturated five-membered or six-membered ring, and R is $C_1$–$C_5$-alkyl, or a salt thereof, is allowed to act on the fungi, or areas, materials, plants, soil or seed threatened by fungus attack.

* * * * *